United States Patent [19]

Braunstein et al.

[11] Patent Number: 6,105,786
[45] Date of Patent: *Aug. 22, 2000

[54] SURFACTANT-BASED EXTRACTION PROCESS

[75] Inventors: Edit L. Braunstein, Rochester, N.Y.; Nathaniel T. Becker, Burlingame, Calif.; Grant C. Ganshaw, Tracy, Calif.; Thomas P. Graycar, Pacifica, Calif.

[73] Assignee: Genencor International, Inc., Rochester, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/887,494

[22] Filed: Jul. 2, 1997

Related U.S. Application Data

[63] Continuation of application No. 08/379,377, Jan. 27, 1995, abandoned.

[51] Int. Cl.$^7$ ............... C11D 7/42; C12S 9/00; C12N 9/00; C12N 9/54
[52] U.S. Cl. ............ 210/392; 210/530; 435/221; 435/183; 435/816
[58] Field of Search ................... 435/816, 221, 435/183; 210/634, 392, 530; 530/422

[56] References Cited

U.S. PATENT DOCUMENTS

| | | | |
|---|---|---|---|
| 4,507,219 | 3/1985 | Hughes | 510/341 |
| 4,578,269 | 3/1986 | Morein | 424/196.11 |
| 4,728,613 | 3/1988 | Brewer et al. | 435/222 |
| 4,992,271 | 2/1991 | Fernandes et al. | 424/85.2 |
| 5,194,639 | 3/1993 | Connor et al. | 554/66 |
| 5,254,339 | 10/1993 | Morein | 424/191.1 |
| 5,271,840 | 12/1993 | Kresheck | 210/634 |

FOREIGN PATENT DOCUMENTS

| | | |
|---|---|---|
| 0 574 050 | 12/1993 | European Pat. Off. . |
| 9623061 | 8/1996 | WIPO . |

OTHER PUBLICATIONS (Item BB) Chemical Abstracts No. 117:107676 (Kitahara, T. et al.) (1991) "Application of Pluronic F68 for aqueous two–phase partition proteins".

Vasudevan, M. et al. (1995) Biotechnology and Bioengineering 46:99–108.

Derwent Abstracts No. 82–04177 (Ferster, M. et al.)(1982) "Application of the two–phase–system aqueous solution Triton X–114 in protein chemistry: extraction of hydrophilic proteins by varying ionic strength and the use of dense sucrose solutions".

Slinde, E. et al. (1976) Eiochimica et Biophysica Acta 445:796–805.

Nikas, Y.J. et al. (1992) 25(18):47974806.

Föster et al. (1982) *Hoppe Seyler Z. Physiol. Chem.*, 363, "Application of the Two–Phase–System Aqueous Solution/ Triton X–114 in Protein Chemistry: Extraction of Hydrophilic Proteins by Varying Ionic Strength and the Use of Dense Sucrose Solutions", pp. 1010–1011.

Holm et al. (1986) *J. Biol. Chem.*, 261(33), "Demonstration of the Amphiphilic Character of Hormone–Sensitive Lipase by Temperature–Induced Phase Separation in Triton X–114 and Charge–Shift Electrophoresis", pp. 15659–15661.

Bordier (1981) *J. Biol. Chem.*, 256(4), "Phase Separation of Integral Membrane Proteins in Triton X–114", pp. 1604–1607.

Terstappen et al. (1992) *Biotechnol. Appl. Biochem.*, 16 (3), "The Use of Detergent–Based Aqueous Two–Phase Systems for the Isolation of Extracellular Proteins: Purification of a Lipase from *Pseudomonas cepacia*", pp. 228–235.

Terstappen et al. (1993) *J. Biotechnol.*, 28(3), "Protein Partitioning in Detergent–Based Aqueous Two–Phase Systems", pp. 263–275.

Kitahara, T., et al., "Application of Pluronic F68 for Aqueous Two–Phase Extraction of Proteins"*J. Chemical Engin. Japan* 26(2) :183–188 (1993).

*Primary Examiner*—Jon P. Weber
*Attorney, Agent, or Firm*—Margaret A. Horn; Kristen A. Anderson; LeeAnn Gorthey

[57] ABSTRACT

A process is disclosed for preparing a detergent powder containing enzymes where the enzymes are extracted from a fermentation broth with a salt and surfactant mixture and directly agglomerated with detergent paste and dried to form the detergent powder. The process results in a two phase system where the enzyme is extracted into the surfactant rich phase and the second phase is salt rich. The process is especially useful for whole or clarified fermentation broths.

6 Claims, 1 Drawing Sheet

SURFACTANT-BASED EXTRACTION PROCESS

This is a Continuation of application Ser. No. 08/379,377 filed Jan. 27, 1995 now abandoned.

FIELD OF THE INVENTION

This invention relates to the recovery or extraction of fermentation products from either clarified or whole fermentation broth utilizing a suitable surfactant. Specifically, this invention relates to surfactant-based extraction of hydrophilic fermentation products.

BACKGROUND OF THE INVENTION

It is well known that many biological products, for example, proteins such as enzymes, are produced by the culturing of certain organisms (yeast, bacteria, fungi) in appropriate nutrient media under suitable conditions. After culturing or fermenting the organisms to produce the desired product, one needs to recover the product from the fermentation broth. This recovery process can be problematic, particularly when done on a large commercial scale. Problems can be encountered due to the large volume of broth produced, the viscosity of the broth, the cells and cellular debris present in the broth, the solubility of the desired product, etc. These problems are well understood by those active in the field.

Many recovery processes for biological/fermentation products have been developed. For example, EP Patent 0 214 531 B1 describes a recovery process for extracellular enzymes from whole fermentation broth comprising adding a mixture of a polymer, such as polyethylene glycol, and a salt. Likewise, U.S. Pat. No. 4,144,130 describes a recovery process for enzymes from intact cells and cell fragments using either a polymer-salt mixture or a multi-polymer system. These processes and many others known in the art are not commercially attractive for large scale recovery of commodity products, primarily because of the need to develop efficient recycling operations for regenerating high cost polymers (extractants) used in such processes, in order to economically recover the products on a continuous basis. EP 0 574 050 A1 discloses methods for recovery and purification of hydrophobic fermentation products. However, this process is useful only for hydrophobic fermentation products and does not employ high HLB surfactants as does the present invention. Therefore, there is a need for a more economical large scale recovery process for recovering products (and particularly hydrophilic products) from fermentation broths.

An improved process has been developed and is described herein, which is a surfactant-based extraction process. This process is particularly useful for the recovery of fermentation products such as enzymes to be used in detergent formulations ("detergent-type enzymes"), because detergent formulations already incorporate a large amount of surfactant. Furthermore, the surfactant-based extraction process is particularly useful for the extraction of hydrophilic products, which heretofore have not been recovered into surfactants by extraction. Thus, for example, one could recover a detergent-type enzyme such as a relatively hydrophilic alkaline protease by extracting the enzyme from its fermentation broth (clarified or whole) using a surfactant which is compatible with the ultimate detergent formulation for which the detergent-type enzyme is destined. This recovery process results not only in very high yields of enzyme recovery, but also in reduction of the overall cost of producing the product since the cost of the surfactant used in the enzyme recovery process is offset by the reduction of necessary surfactant to be added by the formulator making the detergent end product.

SUMMARY OF THE INVENTION

In accordance with the present invention there is provided a process for the extraction of a desired fermentation product from either clarified or whole fermentation broth, the process comprising:

a) contacting a clarified or whole fermentation broth comprising the desired fermentation product with one or more salt(s) and a suitable surfactant having a hydrophile-lipophile balance of at least about 12;

b) separating the fermentation broth into two phases, a first phase comprising the desired product and the surfactant (surfactant-rich phase) and a second phase comprising the salt (salt-rich phase); and c) recovering the first surfactant-rich phase;

d) optionally separating the surfactant from the desired product.

In a preferred embodiment of the present invention, the desired fermentation product is a hydrophilic enzyme (as defined herein), more preferably the desired fermentation product is a hydrophilic detergent-type enzyme such as a protease, amylase, cellulase or cellulase component, or endoglycosidase. These enzymes are commonly added to standard cleaning product formulations to enhance the cleaning activity of the products. Such cleaning products also typically comprise a substantial amount of anionic, cationic or non-ionic surfactants (detergents); therefore, it is preferred that the surfactant used in the present recovery process be compatible with or useful in the end detergent product.

In another embodiment of the invention there is provided a process as set forth above, wherein the process can be used on any fermentation product (hydrophilic or hydrophobic) provided that the surfactant employed has an HLB greater than about 15.

Advantageously, the process of the present invention comprises a single-step extraction process wherein after the addition of the salt and surfactant the fermentation broth separates into two phases, a surfactant-rich phase and a salt-rich phase. The desired product is substantially found in the surfactant-rich phase.

DETAILED DESCRIPTION OF THE INVENTION

Figure 1:
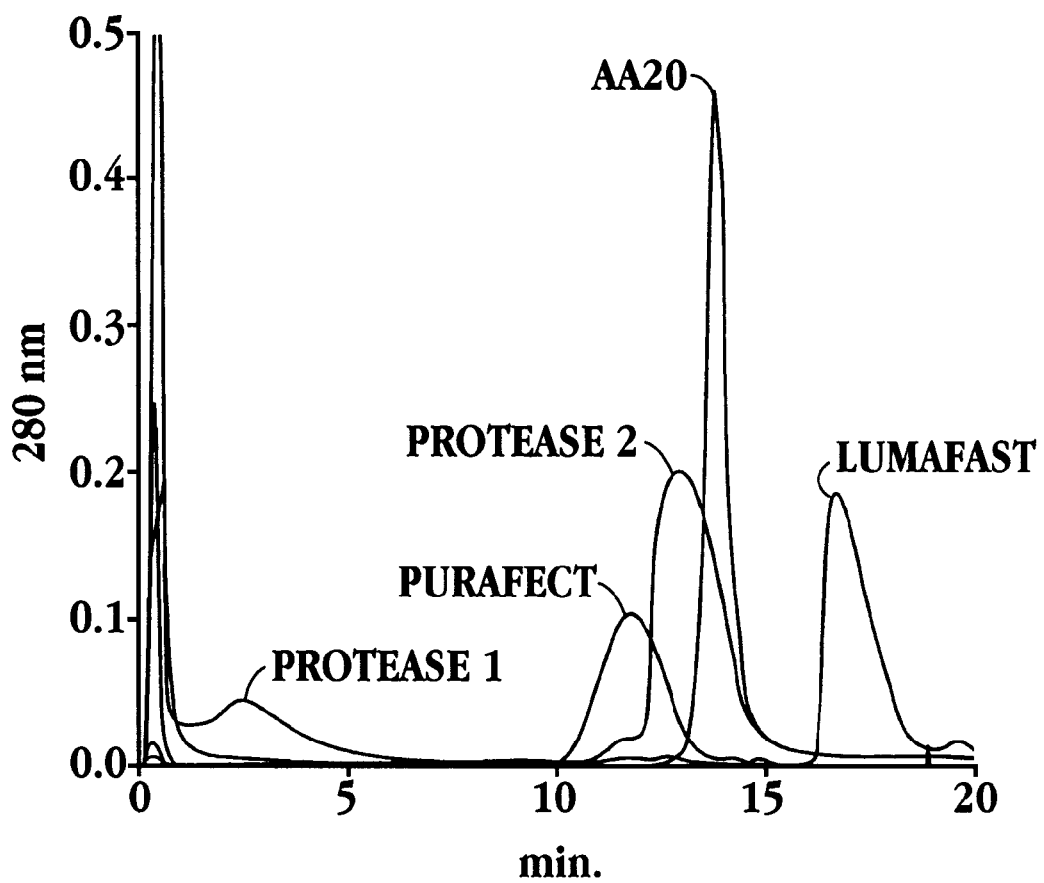
FIG. 1 shows the overlaid traces of various enzyme samples measuring the retention time (min.) of such enzyme samples from a hydrophobic interaction chromatograph (HIC) column under high salt conditions.

As used herein, "detergent-type enzymes" means any enzyme which may be useful in a cleaning product such as a laundry detergent, a hard surface cleaner, a personal care cleaning product, dishcare products, etc. Thus, detergent-type enzymes include, but are not limited to, proteases, cellulases, amylases, endoglycosidases, lipases, peroxidases, laccases, catalases, etc.

As used herein, "hydrophilic" means the relative hydrophilicity of a desired product as measured by the retention time of the product on a HIC resin under conditions such as set forth in Example 1. For purposes of this invention, a product having a retention time of less than about 14 mins. as measured on a HIC column under high salt conditions is deemed hydrophilic. Generally, HIC is a method for testing the relative hydrophobicity/hydrophilicity of a protein (enzyme) wherein the enzyme remains structurally intact and only the exposed surface of the enzyme interacts with the resin and mobile phase. This procedure involves salting out the enzyme onto an uncharged HIC resin, typically a phenyl or alkyl ligand, and eluting the enzyme by using a decreasing salt gradient to reduce the interaction with the resin. Thus, the enzyme will stay bound to the resin as long as the solvent has a lower degree of interaction with the enzyme. Therefore, the longer the enzyme stays bound to the hydrophobic matrix (in an environment of decreasing salts), the less hydrophilic the surface of the enzyme. Conversely, the more quickley the protein is released from the column, the more hydrophilic the protein.

As used herein, "hydrophile-lipophile balance," or HLB, is a quantitative measure of the overall hydrophilic nature of a given surfactant. As the HLB of a surfactant increases, so does the overall hydrophilic nature of the surfactant. This is a term readily understood by those skilled in the art and can be calculated, for example, on the basis of the following.

The HLB for a nonionic polyhydric alcohol fatty acid is defined as:

$$HLB=20(1-S/A)$$

where

S=saponification number of the ester=mg KOH to neutralize 1 g fat

A=acid number of the acid=mg KOH to neutralize 1 g acid or $$HLB=(E+P)/5$$

where

E=weight percentage of oxyethylene content

P=weight percentage of polyhydric alcohol content

This has been extended to other hydrophilic and hydrophobic groups where $$HLB=7+sum\ (hydrophilic+hydrophobic\ group\ numbers)$$

where

|  | Group | Group Number |
|---|---|---|
| hydrophilic | —SO$_4$Na | 38.7 |
|  | —COOK | 21.1 |
|  | —sulfonate | 11 |
|  | —sorbitan ester | 6.8 |
|  | —free ester | 2.4 |
|  | —COOH | 2.1 |
|  | —OH | 1.9 |
|  | ether | 1.3 |
|  | tertiary amine | 9.4 |
| hydrophobic | —CH—, —CH$_2$—, CH$_3$—, —CH— | 0.475 |
| derived | —(CH$_2$—CH$_2$—O)— | 0.33 |
|  | —(CH$_2$—CH$_2$—CH$_2$—O)— | -0.15 |

These and related rules have been used to derive the HLB values published in McCutcheon's, Vol.1, Emulsifiers and Detergents, North American Edition, 1993.

Applicants' invention provides a surfactant-based extraction system whereby hydrophilic proteins (enzymes) can be extracted at high (greater than about 50%, preferably greater than about 80%) yields utilizing a surfactant having an HLB greater than about 12, preferably greater than or equal to about 15. In contrast to the present discovery, those skilled in the art have tried to extract proteins using moderate HLB surfactants based on the knowledge that a moderate HLB surfactant (Triton X-100®) is useful for extracting membrane bound proteins. Bordier, C., Journal of Biol. Chem., Vol. 256, No. 4, pp.1604–1607 (1981). Additionally, the use of low or moderate HLB surfactants (as compared to the high HLB surfactants of applicants' invention) have been reported in findings relating to cloud point extraction using low or moderate HLB surfactants, whereby a spontaneous separation into separate phases occurs at elevated temperatures (Kula, et al., Biotechn. Appl. Biochem. (1992) 16(3) :228–235). As used herein, low HLB means an HLB of less than 8, moderate HLB means an HLB of between 8 and 12 and high HLB means an HLB of greater than 12, preferably greater than about 15.

Also, in contrast to the present invention, work in this area has primarily focused on the extraction of hydrophobic proteins such as lipase (see, for example, EP 0 574,050 A1 and Kula, et al., J. Biotechnol. (1993) 29(2–3):263–275). Conversely, the present invention teaches a method useful for the extraction of hydrophilic proteins (proteins having a retention time of less than about 14 minutes on a HIC column), as well as a general extraction process useful for any protein (regardless of retention time) provided the HLB of the surfactant used is greater than about 15.

Whole fermentation broth containing either extracellular or intracellular products such as enzymes, or a mixture of each, as well as the cells from the starting organisms and/or cell fragments collectively referred to as "cellular debris," can be used without further processing in the recovery process of the present invention. Alternatively, the fermentation broth may first be clarified/purified by known methods such as ultrafiltration to remove all or substantially all of the cellular debris. When the whole fermentation broth is used, one may chose to dilute the broth prior to initiating the recovery process. Such a dilution may be performed by adding water in order to reduce the total solids percentage in which the desired product could be entrained, and to reduce the viscosity or conductivity of the broth prior to separation.

The whole broth or clarified broth is mixed with a salt and surfactant to form a two-phase system. The desired product (e.g., enzyme) will collect in the surfactant-rich phase while the remaining undesired by-products, such as the cellular debris, secondary enzymes, carbohydrates, etc., will collect in the salt-rich phase. This separation allows the efficient, high yield recovery of the desired product.

Salts useful in the present invention can be any known to those skilled in the art, and particularly those compounds wherein the cations are monovalent or divalent metal ions such as sodium, potassium, magnesium, ammonium, aluminum and calcium, and the anions are polar oxygenated ions, including but not limited to, sulfates, carbonates, phosphates, acetates, formates, nitrates and citrates, or halides, including but not limited to, chlorides, bromides and iodides, and mixtures thereof. Preferred salts include, but are not limited to, sodium sulfate, sodium phosphate, sodium chloride and sodium formate.

Suitable surfactants useful in the present invention include any non-ionic surfactant having an HLB of at least about 12, including but not limited to: octylphenol polyether alcohols (such as Triton X®-100, X-165, X-305 or X-405, commercially available from Rohm & Haas), nonylphenol polyether alcohols (such as Armul 930® (Witcho Corp.), Alka Surf NP-15® (Rhone Poulenc), Carsonon N-30® (Lonza, Inc.), Cedepal CO-730® (Stepan Canada, Inc.), etc.), alcohol ethoxylates (such as Neodol® 91-6, 91-8, 23-6.5, 25-12, 45-13 or 25-20, commercially available from Shell). Suitable surfactants are described in McCutcheon's, Vol.1, Emulsifiers and Detergents, North American Edition, 1993, a standard catalog of commercial surfactants. Preferred surfactants of the present invention include those surfactants having an HLB of at least about 15, for example, Triton X-165®, Triton X-305®, Triton X-405® and the like.

When the desired fermentation product to be recovered by the extraction process of the present invention is a detergent-type enzyme, the preferred surfactant is a surfactant compatible with the detergent formulation into which the detergent-type enzyme will be incorporated. Such detergent formulation surfactants are described in U.S. Pat. No. 5,194,639 and 4,507,219, which are incorporated herein by reference. U.S. Pat. No. 5,194,639 discloses that nonionic surfactants reported in the literature for use in detergent formulations include ethylene oxide derivatives of fatty alcohols, ethoxylated alcohols, ethoxylated alkyl phenols, and polyhydroxy fatty acid amides.

The recovery process of the present invention contemplates a system whereby an artisan, knowing the relative hydrophilic nature of the desired fermentation product to be recovered (as measured by retention time on HIC), can utilize a given surfactant having a hydrophile-lipophile balance (HLB) of at least about 12. Preferably as the hydrophilic nature of the desired product increases (has reduced retention time), the surfactant selected may require an increased HLB (i.e., greater than about 15) to maximize the yield. Generally, surfactants of higher HLB will increase extraction yields for most proteins but will also result in less selective extraction.

HLB values of surfactants are available from the commercial suppliers of such products, for example, Triton X-100® has an HLB of 13.5. The higher the HLB value, the more hydrophilic the surfactant. Preferred surfactants useful in the present invention, depending, of course, on the nature of the product to be recovered, will have an HLB of at least about 12, and preferably at least about 15. Thus, for the high yield recovery of a hydrophilic enzyme such as an alkaline protease (having a retention time of less than 14 mins. on a HIC column), one would select a surfactant having a high HLB. (i.e.,$\geq$12.0). Furthermore, for the high yield recovery of a more hydrophilic enzyme (i.e., having a retention time of less than 4 mins. on a HIC column), one would select a surfactant having a higher HLB (i.e.,$\geq$15).

Additionally, the phenomenon of high yield surfactant extraction of more hydrophobic proteins has also been demonstrated by the present invention. Thus, if a given protein is relatively hydrophobic (i.e., has a retention time of greater than about 14 mins.), the protein can still be extracted in high yields (>50%, preferably >80%) provided a surfactant having an HLB of at least about 15 is employed.

The salt(s) and surfactant are added to the fermentation broth (whole or clarified) at a temperature from about room temperature to about 40° C. The salt is typically added first since the dissolution of the salt may require warming and/or stirring of the fermentation broth. However, the surfactant can be added prior to the salt. The addition of the salt and surfactant can be made over a broad pH range (2–10 pH) depending on the nature of the fermentation product to be recovered. The additions of salt and surfactant may be made with or without stirring.

After addition of the salt and surfactant, typically the fermentation broth will separate such that two phases will form, however, it is possible that a third (interfacial) phase will be formed. If this third interfacial phase is present, it should be treated as part of the top or surfactant-rich phase. The surfactant-rich phase will typically be the top phase and will comprise the desired product. The two phase separation can be formed or occur by settling, whereby the mixture is allowed to stand without stirring, or, conversely, the separation may be achieved by centrifuging the mixture by methods known to those skilled in the art. It is preferable that the surfactant-rich phase be substantially free of the salt-rich phase. By substantially free it is meant that little or none of the salt-rich phase or other undesirable by-products (such as cellular debris, secondary enzymes, carbohydrates, etc.) are entrained within the surfactant-rich phase. Likewise, it is preferable that substantially all the desired product is entrained within the surfactant-rich phase. These factors can be monitored by measuring the volume split and partition coefficient of the recovery process. The volume split is calculated by dividing the volume of the top (surfactant) phase by the volume of the bottom (salt) phase. This volume split should preferably be low (0.1 to 0.5) because that will result in a more concentrated material. The partition coefficient (K) is calculated as the ratio of the enzyme concentration in the top (surfactant) phase and the enzyme concentration in the bottom (salt) phase. The partition coefficient is preferably high (>5) because it is typically desirable to have the product selectively enriched into the surfactant-rich phase.

The surfactant-rich phase (substantially free of the salt-rich phase) is then collected or recovered by methods known to those skilled in the art including, for example, by centrifugation. As such, the desired product is now recovered in the surfactant-rich phase. This surfactant/desired product phase can be formulated directly into the desired product. For example, a surfactant-alkaline protease phase can be used directly in a detergent formulation, provided that the surfactant is compatible with the given detergent formulation. On the other hand, if the desired product is not to be used in conjunction with a surfactant (for example, if the desired product is a recombinant rennin/chymosin product), the product can be separated from the surfactant by well known techniques, such as precipitation, ultrafiltration, back extraction, chromatography or evaporation, to produce a substantially surfactant-free product.

Extraction of a fermentation product by the presently described methods may be carried out so as to result in a highly viscous material, suitable for direct agglomeration into solid products such as detergent powders.

Preferably the desired products of the present invention are detergent-type enzymes. As used herein, detergent-type enzyme means any enzyme which is useful in a detergent-based cleaning product. These include, but are not limited to, proteases, cellulases (or components thereof), amylases, lipases, endoglycosidases, laccases, peroxidases, catalases, etc., or any combination of these enzymes. Specifically useful enzymes include, but are not limited to: alkaline proteases such as Purafect® or Purafect® OxP (both commercially available from Genencor International, Inc.), Savinase™ (commercially available from Novo Industries), protein engineered enzymes such as Protease 899 (commercially available from Genencor International, Inc.), Durazym™ (a protease comprising +195 and +222 mutations, commercially available from Novo Nordisk A/S), Maxapem™ (a protease comprising a +222 mutation, commercially available from Gist-brocades); amylases such as Spezyme® (commercially available from Genencor International Inc.) or protein engineered amylases such as described in U.S. patent application Ser. Nos. 08/194,664 and 08/289,3521 (incorporated herein by reference); cellulases or cellulase components such as Denimex™ (commercially available from Novo Nordisk A/S) or Trichoderma-like cellulases and cellulase components as described in U.S. patent application Ser. No. 07/707,647 and U.S. Pat. No. 5,120,463, the disclosure of which are incorporated herein by reference; lipases such as Lumafast® (commercially available from Genencor International, Inc.) or Lipolase™ (commercially available from Novo Nordisk A/S); or endoglycosidases such as those described in U.S. Pat. Nos. 5,238,843 and 5,258,304.

As described, one advantage of the present invention is to recover the desired fermentation product, preferably an enzyme, into a surfactant-rich phase which can be used directly as the enzyme source for a given surfactant-containing end product. When a detergent-type enzyme is the desired fermentation product, the enzyme may be incorporated into known detergent or cleaning product formulations. Detergent or cleaning product formulations include, but are not limited to, any industrial or consumer cleaning product such as laundry products, hard surface cleaners, laundry pre-treatment products, dishcare products, personal hygiene products, etc. These products may be liquid or powdered. The skilled artisan is familiar with different formulations which can be used as cleaning compositions. A number of known compounds are suitable surfactants useful in compositions containing enzymes. Examples of such cleaning formulations are described in U.S. Pat. Nos. 4,404,128 and 4,261,868, which are incorporated herein by reference.

It is further contemplated that after separation of the desired product into a surfactant-rich phase, one may wish to further separate the desired product from the surfactant. For example, if one were to use the present process to recover an enzyme useful as a diagnostic aid or research reagent (for example, an endoglycosidase such as PNGase F, described in U.S. Pat. No. 5,238,843), it may be desirable to further recover the PNGase F from the surfactant and to purify the enzyme by methods known to those skilled in the art.

The following examples are for illustrative purposes only and are not intended to limit the scope of the present invention.

Experimental

EXAMPLE 1

Determining the Relative Hydrophilicity of a Product to be Recovered

Where the hydrophilic nature of the product to be recovered by the present invention is unknown, it may be necessary to determine such in order to choose an appropriate surfactant.

In the case of the following examples, the hydrophilicity of each enzyme to be recovered was determined by hydrophobic interaction chromatography (HIC). The details of the specific methodology used herein to calculate retention time (as a measure of hydrophobicity) are provided below as are the results achieved.

Materials and Methods

Using PD-10 columns (Pharmacia Biotech) and 20 mM sodium acetate and 5 mM calcium chloride buffer at pH 5.2, a liquid volume of the formulated ultrafiltered enzyme concentrate containing at least 25 mg of the enzyme to be tested was applied to an equilibrated PD-10 column (the volume added is limited to 2.5 mL per column). The enzyme sample was eluted from the PD-10 column with 3.5 mL of the acetate buffer and then split into 2 aliquots (1.75 mL each) which were applied to 2 freshly equilibrated PD-10 columns (1.75 mL/column) and eluted in the same manner as before. This procedure resulted in 7 mLs of desalted enzyme sample in a common matrix. Ammonium sulfate was added to this 7 mL pool of enzyme to bring the concentration of ammonium sulfate in the sample to approximately 1.5M (the ammonium sulfate can be added as either a liquid volume from a 4M solution or as a solid granular form to the desalted sample at room temperature while mixing). During the addition of ammonium sulfate to the enzyme sample, the enzyme may start to precipitate and the solution will turn cloudy. If this clouding occurs, discontinue the addition of ammonium sulfate and dilute the sample with acetate buffer to eliminate the cloudiness.

The enzyme sample was then applied to the HIC column using a sufficient volume (determined by appropriate enzyme assay) to yield a 5 mg load. The analysis of the sample required the capability of developing and delivering a gradient, as well as allowing for the injection of sample on a column. Therefore, a BioCAD 60 ® (PerSeptive Biosystems) was used, although a FPLC by Pharmacia Biotech could be used. When dealing with enzymes of unknown hydrophobicity, a low substitution phenyl column was used (a phenyl ligand bonded to a support matrix). In this experiment a POROS PH/M ® column (4.6×100 mm, 20 micron particle size) (PerSeptive Biosystems) was used but similar columns are available from other vendors, e.g., Phenyl Superose HR 5/5® (Pharmacia Biotech). Flow from the column was monitored with an appropriate detector at 280 nm (this should be connected to a chart recorder to chart the progress of the increase/decrease of absorbance seen in the column eluent) for presence of the enzyme.

Fractions were collected starting at and continuing onward from the point of sample injection, so that the presence of enzyme could be visualized at the point of elution and defined by applying an appropriate assay of the fractions. The running buffer used was 1.5M ammonium sulfate in 50 mM sodium phosphate at pH 7.0, with the eluting buffer as ultrapure water. A flow rate compatible with the column being used (in the case of POROS PH/M®, 10 mL/min.) was used to run 20 cv (column volumes) of running buffer through the column followed by the application of the appropriate volume of prepared sample (to get a 5 mg load). The flow rate was then reduced to 75% of the initial rate and the column (containing enzyme sample) was washed with the running buffer for 25 cv.

Elution of the enzyme from the column was accomplished by running at the same flow rate (75% of initial) and developing a gradient from the running buffer to 100% of ultrapure water. Conductivity was measured on the enzyme samples loaded and compared to the conductivity of the running buffer during elution, and the peak elution times were noted. The higher the eluate conductivity and the earlier the elution, the less hydrophobic is the enzyme. Several runs were made and compared to ensure that the data was relevant to the conditions involved.

Enzyme Samples: Formulated UF concentrate of each enzyme was used. The enzymes tested include:

Protease 1, a modified alkaline protease from *Bacillus amyloliquefaciens* expressed in *B. subtilis*, as described in U.S. Pat. No. RE 34,606. This enzyme is commercially available as Protease 899 from Genencor International, Inc.

Protease 2, a modified alkaline protease from *Bacillus lentus* expressed in *B. subtilis*, as described in U.S. Pat. No. 5,185,258.

Purafect, a protease from *B. lentus* commercially available from Genencor International, Inc.

AA20, a *Bacillus licheniformis* alpha-amylase enzyme commercially available as SPEZYME AA20 from Genencor International, Inc.

Lumafast(®), a *Pseudomonas mendocina* cutinase, as described in U.S. Pat. No. 5,352,594 and commercially available from Genencor International, Inc.

Formulated UF concentrated samples of Proteases 1 and 2, Purafect®, AA20 and Lumafast® were desalted using PD-10 (Pharmacia Biotech) desalting columns, adjusted to 1.5 ammonium sulfate concentration with 4M ammonium sulfate and assayed for enzyme concentration using an appropriate enzyme assay.

The data from 3 runs for each enzyme sample were collected and averaged. Results of the 3 runs are shown in Table 1 and in FIG. 1. As noted previously, an enzyme which elutes at a high conductivity (high salt concentration) has a lower association with the hydrophobic matrix of the column than that of an enzyme which elutes in lower conductivity (lower salt concentration). In the present example it can be seen that an early eluting enzyme is less hydrophobic than a later eluting enzyme. Thus, by comparison as to hydrophilicity, the ranking from least hydrophilic to most is: Lumafast<AA20<Protease 2<Purafect<Protease 1.

EXAMPLE 3

In a manner similar to the extraction procedure described in Example 2 above, Protease 2 was extracted using Neodol 91-6 (ethoxylate non-ionic surfactant with an HLB of 12.5, commercially available from Shell) with the following results:

| | |
|---|---|
| Volume Split | 0.22 |
| Partition Coefficient | 57 |
| Concentration Factor | 4.66 |
| Yield Top Phase | 100 |

From the above data it is apparent that the process of this invention permits the efficient recovery of alkaline proteases, using various surfactants having HLB>12.

EXAMPLE 4

In this example the filtrated broth containing Protease 1 (Protease 899, commercially available from Genencor International, Inc.) was used for the surfactant-based extraction.

To 10 ml of filtrate at pH 7.33, 17 grams of sodium sulfate and 10 grams of sodium chloride were added. The material

TABLE 1

| Peak Name/Enzyme | Retention Time (min.) | Salts in Buffer (% A) | Water (% C) | Conductivity (mS) | Enzyme (Peak Area %) | Unretained Load (Peak Area %) | Total Recovered (Peak Area %) |
|---|---|---|---|---|---|---|---|
| Protease 1 | 2.75 | 100.00 | 0.00 | 105.45 | 41.12 | 58.88 | 100.00 |
| Protease 2 | 12.89 | 64.16 | 35.84 | 87.20 | 77.32 | 22.68 | 100.00 |
| Purafect ® | 11.78 | 78.01 | 21.99 | 99.28 | 75.30 | 24.70 | 100.00 |
| AA20 | 13.75 | 56.33 | 43.67 | 76.45 | 94.75 | 0.90 | 95.65 |
| Lumafast ® | 16.38 | 32.68 | 67.32 | 52.36 | 83.02 | 1.82 | 84.84 |

EXAMPLE 2

A fermentation of Protease 2 (a subtilisin as described in U.S. Pat. No. 5,185,258) expressed in *B. subtilis* was carried out. The fermentation broth was clarified by flocculation of the biomass and filtration through a rotary vacuum drum filter (RVDF).

100 ml of filtrate was adjusted to pH 7 with formic acid. 15 grams of sodium sulfate and 10 grams of sodium chloride were added to the filtrate. The material was then warmed to 25° C. and mixed for about 1 hour to dissolve all of the salt. 10 ml of Triton X-100® (non-ionic octylphenol polyether alcohol, commercially available from Rohm & Haas) with an hydrophile-lipophile balance (HLB) value of 13.5 was added and mixed for about 15 minutes. The mixture was separated into two phases (a top phase rich in the surfactant and a bottom phase rich in salts) by centrifugation (IEC Centra-β® Centrifuge) at about 3000 g for about 15 minutes, and the phases were assayed for subtilisin activity.

The volume split (volume of the top phase/volume of the bottom phase) was calculated to be 0.2. The partition coefficient (ratio of the enzyme concentration in the top phase/enzyme concentration in the bottom phase) was calculated to be 442. The concentration factor (which is the relation between the enzyme concentration on the top phase and the original concentration) was calculated to be 4.7. The yield of the extraction (which is the ratio between the total enzyme recovered in the top phase and the initial quantity) was calculated to be 93%.

was mixed for about one hour at about 35° C. The material was then distributed into 15 ml centrifuge tubes by transferring 9 ml to each tube.

To the tubes, 1 ml of three different non-ionic surfactants with different HLB values were added. The tubes were mixed and placed in the centrifuge for separation into the two phases, and the phases assayed for subtilisin activity. The results are as follows:

| Surfactant | Surfactant HLB | Volume Split | Partition Coefficient | Concentration Factor | Yield |
|---|---|---|---|---|---|
| Triton X-100 | 13.5 | 0.2 | 0.81 | 0.7 | 15% |
| Triton X-165 | 15.8 | 0.13 | 4.17 | 3.65 | 49% |
| Triton X-305 | 17.3 | 0.24 | 8.93 | 3.1 | 69% |
| Triton X-405 | 17.9 | 0.18 | 53 | 6.63 | 100% |

From the data set forth above, it can be seen that as the HLB of the surfactant increases, the recovery (% yield) of a very hydrophilic enzyme such as Protease 1 (retention time=2.75 min.) can be enhanced. By comparison with Protease 2 in Example 3, which is more hydrophobic (retention time=12.89 min.), Protease 1 does not extract at high yield with surfactant of HLB <15. Thus, one may optimize the extraction process by selecting an appropriate surfactant based on the HLB of the surfactant in correlation to the hydrophilic nature of the desired product, as measured by its retention time on a HIC column.

EXAMPLE 5

Whole fermentation broth containing Protease 2 was extracted using the surfactant-based system.

1400 ml of whole broth was added to 700 ml of distilled water and mixed. The material was brought to pH 7 with formic acid. 315 grams of sodium sulfate (15%) and 210 grams of sodium chloride were added and mixed for one hour while the material was warmed to 35° C. to facilitate the dissolution of the salts. Non-ionic surfactant Neodol 91-6® (HLB 13.5) was added to a final concentration of 7.5%.

The prepared mixture was extracted using the Westfalia Continuous Extractor (Model TA-05-00-105). The flow rate used was 180 ml/min. The top and bottom phases were collected and analyzed. The following results were obtained:

| | |
|---|---|
| Volume Split | 0.20 |
| Partition Coefficient | 154 |
| Concentration Factor | 7.8 |
| Yield Top Phase | 100 |

From the above results it can be seen that the extraction process can be scaled up more than 500 times with great efficiency. This also demonstrates the possibility of using a single step operation for recovering and concentration of the enzyme directly from whole broth.

EXAMPLE 6

In this example a protease (Purafect, commercially available from Genencor International, Inc.) contained in whole broth media was extracted by first diluting the material with 50% of distilled water. To 100 ml of material at pH 8 (adjusted to 8 with NaOH), 10 g of sodium sulfate and 10 g of sodium formate were added and mixed for about 1 hour at about 35° C.

After the mixing the material was transferred to 15 ml test tubes, which contained 375 ul (7.5% final volume) of Neodol 91-6® (HLB 12.5), to a final volume of 5 ml. The tubes were spun in the lab top centrifuge at 3500 rpm for 15 minutes. Two phases were obtained, the top phase containing the desired protease. Calculations of the different parameters were performed and the results were as follows:

| | |
|---|---|
| Volume Split | 0.12 |
| Partition Coefficient | 38 |
| Concentration Factor | 14 |
| Yield Top Phase | 100 |

EXAMPLE 7

In this example the cell-free broth containing a *P. mendocina* lipase (Lumafast®, commercially available from Genencor International, Inc.) was treated with sodium sulfate and sodium chloride at 15% (w/volume) of each, mixed for about 1 hour at 35° C., then the salt-containing material was transferred to 15 ml test tubes containing 400 ul of three different Tritons: X-100, X-305 and X-405, to a final volume of 4 ml. The tubes were spun at 3500 rpm for 15 minutes, the volume of the phases was determined and the phases were assayed for lipase activity. With these data the yield on the top phase was determined. The following results were obtained.

| Triton | HLB | Recovered Yield |
|---|---|---|
| X-100 | 13.5 | 87% |
| X-305 | 17.3 | 98% |
| X-405 | 17.9 | 100% |

It can be seen that with this enzyme, which has a more hydrophobic enzyme retention time of 16 mins. as per Example 1, high yields were achieved when a surfactant having an HLB even as low as 13.5 was used. Yet, as the HLB of the surfactant increased, the percent yield continued to increase.

EXAMPLE 8

A surfactant extract of alkaline protease is prepared by the process described in Example 3, except that the extraction is run using 5–10% of the Neodol surfactant (HLB 12.5), such that the extract has the consistency of a paste, not a free-flowing liquid. Where a liquid extract is desired, 10% surfactant should be used.

The extract paste with a protease concentration of 4% w/w is then added to a high shear agglomerator (such as made by Lodige or Shugi) together with a base detergent paste mixture consisting of anionic surfactants (linear alkylbenzene sulfonate, alkyl sulfate, alkyl ethoxy sulfate) and nonionic surfactants (alkyl ethoxylated alcohols). The extract is added typically at 1% of the weight of the base detergent mixture, but could be added at from 0.1% to 10% of this level.

After agglomeration by operating the blades at high speed for 0.25 to 10 minutes, the enzyme-containing surfactant agglomerate is removed as a flowable, granular detergent powder.

The agglomerate has the cost and processing advantages of obviating the need for separate granulation of enzyme, and handling of a granulated enzyme admix. Such enzyme granulation technologies are known to those skilled in the art. Commercial agglomerators for handling surfactant pastes can easily handle the enzyme-surfactant paste (or liquid). Further, the concentration of enzyme in the agglomerated detergent is 10–200× lower than that found in commercial enzyme granules, so that the risk of exposure to sensitizing enzyme dusts is reduced, since it is proportional to the enzyme concentration of the material being handled.

What is claimed is:

1. A process for making a detergent powder containing a surfactant-extracted enzyme, the process comprising:
    a) extracting the enzyme as a paste or liquid from a clarified or whole fermentation broth comprising the desired enzyme by
        i) contacting the broth with one or more salts and a suitable surfactant having a hydrophile-lipophile balance of at least about 12, wherein said salt has a monovalent or divalent metal cation and a halide or polar oxygenated anion;
        ii) separating the fermentation broth into two phases, a first surfactant-rich phase, and a second salt-rich phase; and
        iii) recovering the first surfactant-rich phase comprising the desired enzyme;
    b) agglomerating the extract with a suitable detergent paste mixture to produce an enzyme containing agglomerate; and
    c) drying the enzyme containing agglomerate to obtain said detergent powder.

2. The process of claim 1 wherein the salt is selected from a salt wherein the cation is selected from the group consisting of sodium, potassium, magnesium, ammonium, aluminum and calcium, and the anion is selected from the group consisting of sulfate, carbonate, chloride, bromide, iodide, phosphate, acetate, formate, nitrate and citrate.

3. The process of claim 2 wherein the salt is sodium sulfate, sodium phosphate, sodium chloride, sodium formate, or a mixture thereof.

4. The process of claim 1 wherein the surfactant has a hydrophile-lipophile balance of at least about 15.

5. The process of claim 1 wherein the surfactant is a non-ionic surfactant.

6. The process of claim 1 wherein whole fermentation broth is used, the process further comprising diluting with water the whole fermentation broth comprising the desired enzyme prior to contacting said whole fermentation broth with one or more salts and suitable surfactant.

* * * * *